(12) United States Patent
Newman

(10) Patent No.: US 9,194,843 B2
(45) Date of Patent: Nov. 24, 2015

(54) METHOD AND APPARATUS FOR MONITORING WIND TURBINE BLADES DURING OPERATION

(71) Applicant: Digital Wind Systems, Inc., West Conshohocken, PA (US)

(72) Inventor: John W. Newman, Newtown Square, PA (US)

(73) Assignee: Digital Wind Systems, Inc., West Conshohocken, PA (US)

( * ) Notice: Subject to any disclaimer, the term of this patent is extended or adjusted under 35 U.S.C. 154(b) by 309 days.

(21) Appl. No.: 13/837,145

(22) Filed: Mar. 15, 2013

(65) Prior Publication Data

US 2014/0260634 A1 Sep. 18, 2014

(51) Int. Cl.
 *G01N 29/22* (2006.01)
 *F03D 11/00* (2006.01)

(52) U.S. Cl.
 CPC ............ *G01N 29/22* (2013.01); *F03D 11/0091* (2013.01); *Y02E 10/722* (2013.01)

(58) Field of Classification Search
 CPC .......... G01N 29/14; G01N 2291/0422; G01N 2291/0258; G01N 29/11; G01N 29/045; G01N 2291/0238; G01N 2291/044; G01N 2291/2696; G01N 2291/02491; G01N 29/30; G01N 29/42; G01N 29/22; G01V 1/001
 USPC .......... 73/587, 645, 584, 593, 602, 596–600, 73/583
 See application file for complete search history.

(56) References Cited

U.S. PATENT DOCUMENTS

| | | | |
|---|---|---|---|
| 3,371,212 A | 2/1968 | Weiss | |
| 3,478,353 A | 11/1969 | Adams, Jr. | |
| 3,810,005 A | 5/1974 | Bennion et al. | |
| 3,922,907 A | 12/1975 | Hurwitz et al. | |
| 4,413,519 A | 11/1983 | Bannister et al. | |
| 4,507,658 A | 3/1985 | Keating | |
| 5,146,289 A | 9/1992 | Newman | |
| 5,257,088 A | 10/1993 | Tyson, II et al. | |
| 5,365,787 A * | 11/1994 | Hernandez et al. | 73/660 |
| 5,479,826 A | 1/1996 | Twerdochlib et al. | |

(Continued)

FOREIGN PATENT DOCUMENTS

| EP | 2131037 A2 | 12/2009 |
|---|---|---|
| EP | 2527649 B1 | 11/2012 |

(Continued)

OTHER PUBLICATIONS

Hung, Y.Y., "Shearography for Non-destructive Evaluation of Composite Structures", Optics and Lasers in Engineering, vol. 24, pp. 161-182, (1996).

(Continued)

*Primary Examiner* — Helen Kwok
(74) *Attorney, Agent, or Firm* — Panitch Schwarze Belisario & Nadel LLP

(57) ABSTRACT

A wind power turbine blade inspection system includes a sensor positioned on the blade root end bulkhead to receive airborne acoustic signals emanating from anomalies in rotating turbine blades during cyclic stress loading, a three axis accelerometer to determine the gravity vector and other sources of cyclic acceleration with respect to the acoustic signals and a signal analysis system configured to analyze the sensor and accelerometer signals to provide data for wind power asset management.

13 Claims, 7 Drawing Sheets

(56) References Cited

U.S. PATENT DOCUMENTS

| | | | |
|---|---|---|---|
| 5,481,356 | A | 1/1996 | Pouet et al. |
| 5,543,916 | A | 8/1996 | Kachanov |
| 5,686,669 | A * | 11/1997 | Hernandez et al. ............ 73/660 |
| 5,748,003 | A | 5/1998 | Zoughi et al. |
| 5,818,242 | A | 10/1998 | Grzybowski et al. |
| 5,923,425 | A | 7/1999 | Dewa et al. |
| 6,153,889 | A | 11/2000 | Jones |
| 6,246,483 | B1 | 6/2001 | Smith |
| 6,301,967 | B1 * | 10/2001 | Donskoy et al. ............... 73/579 |
| 6,394,646 | B1 | 5/2002 | Ringermacher et al. |
| 6,448,924 | B1 | 9/2002 | Hafer, Jr. |
| 6,674,531 | B2 | 1/2004 | Mahner |
| 6,717,681 | B1 | 4/2004 | Bard et al. |
| 6,779,404 | B1 * | 8/2004 | Brincker et al. ............... 73/659 |
| 6,881,507 | B2 | 4/2005 | Milacic |
| 6,891,148 | B1 | 5/2005 | Rivera et al. |
| 6,966,754 | B2 | 11/2005 | Wobben |
| 6,968,730 | B2 | 11/2005 | Schafrik et al. |
| 7,019,537 | B2 | 3/2006 | Hazel et al. |
| 7,083,327 | B1 | 8/2006 | Shepard |
| 7,083,384 | B2 | 8/2006 | Bosselmann et al. |
| 7,095,221 | B2 | 8/2006 | Bosselmann et al. |
| 7,283,251 | B1 | 10/2007 | Tansey |
| 7,432,505 | B2 | 10/2008 | Brummel |
| 7,554,324 | B2 | 6/2009 | Gualtieri |
| 7,825,669 | B2 | 11/2010 | Parsons et al. |
| 7,889,119 | B2 | 2/2011 | Evers et al. |
| 8,120,522 | B2 | 2/2012 | Tralshawala et al. |
| 8,174,139 | B1 | 5/2012 | Parsche et al. |
| 8,553,233 | B2 | 10/2013 | Newman |
| 2001/0050772 | A1 | 12/2001 | Meinlschmidt et al. |
| 2004/0236538 | A1 | 11/2004 | Wobben |
| 2005/0157313 | A1 | 7/2005 | Mendlovic et al. |
| 2005/0167596 | A1 * | 8/2005 | Rothenfusser et al. ..... 250/341.6 |
| 2005/0210983 | A1 * | 9/2005 | Klein et al. ..................... 73/627 |
| 2006/0181285 | A1 | 8/2006 | Friedman et al. |
| 2007/0132461 | A1 | 6/2007 | Holmquist et al. |
| 2008/0237466 | A1 | 10/2008 | Key |
| 2008/0279686 | A1 * | 11/2008 | Demtroder ...................... 416/61 |
| 2009/0201971 | A1 | 8/2009 | Goldammer et al. |
| 2010/0030493 | A1 * | 2/2010 | Rao ................................. 702/39 |
| 2010/0103260 | A1 | 4/2010 | Williams |
| 2010/0253569 | A1 | 10/2010 | Stiesdal |
| 2011/0020122 | A1 * | 1/2011 | Parthasarathy et al. ......... 416/61 |
| 2011/0230304 | A1 * | 9/2011 | Morel ........................... 475/331 |
| 2011/0265575 | A1 * | 11/2011 | Koste et al. ..................... 73/660 |
| 2012/0029840 | A1 | 2/2012 | George |
| 2012/0068462 | A1 * | 3/2012 | Laurberg ........................ 290/44 |
| 2012/0141275 | A1 | 6/2012 | Hiremath et al. |
| 2012/0253697 | A1 | 10/2012 | Frankenstein et al. |

FOREIGN PATENT DOCUMENTS

| | | |
|---|---|---|
| GB | 2235604 A | 6/1991 |
| WO | 2007085259 A1 | 8/2007 |
| WO | 2012003372 A2 | 1/2012 |

OTHER PUBLICATIONS

Meinlschmidt, P., et al., "Thermographic Inspection of Rotor Blades", ECNDT 2006—Tu.1.5.3 (2006).

Leblanc, B., et al., "Full-Field Inspection of a Wind Turbine Blade Using Three-Dimensional Digital Image Correlation", Industrial and Commercial Applications of Smart Structures Technologies 2011, Proceedings of the SPIE, vol. 7979, pp. 79790L-79790L-12, (Mar. 2011).

Bond, L., et al., "Condition Monitoring Techniques for Composite Wind Turbine Blades", Review of Progress in Quantitative Nondestructive Evaluation, vol. 11B, Proceedings of the 18th Annual Review, Brunswick, ME, Jul. 28-Aug. 2, 1991, pp. 1647-1654 (1992).

Jungert, A., "Damage Detection in Wind Turbine Blades Using Two Different Acoustic Techniques", NDT.net—The e-Journal of Nondestructive Testing (Dec. 2008).

Beattie, A., "Non-Destructive Evaluation of Wind Turbine Blades Using an Infrared Camera", American Institute of Aeronautics and Astronautics, AIAA 99-0046, (1998).

Renshaw, J., et al., The Sources of Heat Generation in Vibrothermography. NDT & E International, vol. 44, Issue 8, pp. 736-739 (Dec. 2011).

Rumsey, M., et al. "Structural Health Monitoring of Wind Turbine Blades".Smart Sensor Phenomena, Technology, Networks, and Systems 2008. Proceedings of the SPIE, vol. 6933, article id. 69330E (2008).

Zell, H., et al., "Wind Turbine Inspection—New Methods of Remote Non-destructive Inspection of Rotorblades", Dewi Magazin No. 40, pp. 14-22 (Feb. 2012).

Anjar, B., et al., "Feasibility Study of Thermal Condition Monitoring and Condition based Maintenance in Wind Turbines", Elforsk Electricity and Power Production, Elforsk rapport 11:19, pp. 1-26 (May 2011).

Rumsey, M., "NDT, CM and SHM of Wind Turbine Blades at the National Labs", 2009 NREL Wind Turbine Condition Monitoring Workshop, Wind and Water Power Technology Laboratories, Albuquerque, NM, (Oct. 2009).

Hyers, R., et al., "Condition Monitoring and Prognosis of Utility Scale Wind Turbines", Energy Materials, vol. 1, No. 3, pp. 187-203 (Sep. 2006).

International Search Report and Written Opinion dated Jul. 8, 2014 for corresponding PCT/US2014/030299 filed Mar. 17, 2014.

* cited by examiner

METHOD AND APPARATUS FOR MONITORING WIND TURBINE BLADES DURING OPERATION

INCORPORATIONS BY REFERENCE

Applicant hereby incorporates by reference, as if set forth fully herein, the entirety of the disclosures of U.S. Nonprovisional patent application Ser. No. 13/731,085, filed Dec. 30, 2012 and having the title METHOD AND APPARATUS FOR THE REMOTE NONDESTRUCTIVE EVALUATION OF AN OBJECT, U.S. Nonprovisional patent application Ser. No. 13/839,908, filed on Mar. 15, 2013 and having the title SYSTEM AND METHOD FOR GROUND BASED INSPECTION OF WIND TURBINE BLADES and U.S. Nonprovisional patent application Ser. No. 13/840,470, filed on Mar. 15, 2013 and having the title NONDESTRUCTIVE ACOUSTIC DOPPLER TESTING OF WIND TURBINES BLADES FROM THE GROUND DURING OPERATION.

BACKGROUND OF THE INVENTION

1. Field of the Invention

The invention relates to a method and apparatus for continuously monitoring wind turbine blades in rotating wind turbine generators for the propagation of latent defects and breaking adhesive bonds.

2. Description of the Related Technology

Due to their large size and extensive surface area and complex shape, wind turbine blades are difficult to non-destructively inspect in the factory. Visual inspection does not see defects below the surface. Thermography inspection techniques are somewhat effective but can give false positives and false negatives due to variations in material thickness and surface emissivity. Angle beam ultrasonic techniques are very slow and may not work through thick carbon fiber spar caps. As a result, blades are installed on towers and put into service with a significant probability of latent manufacturing defects. Furthermore, composite blades are subject seasonal temperature variations and entrapped water can undergo freeze/thaw cycles causing internal damage. Cyclic forces of gravity and varying forces from the wind acting on the blades as they rotate can cause fatigue damage or the propagation of latent defects over time.

Detecting progressive damage and propagating defects in wind turbine blades in situ is difficult. Inspectors using sky cranes or rope access are expensive, time consuming and put personnel in a very dangerous working environment. While uptower, close access allows inspectors to visually detect blade trailing edge splits, cracks, lightning damage and blade erosion, such inspections are intermittent, expensive and subjective.

The blades of commercial wind turbines are often several hundred feet off the ground. Access to wind turbine blades in situ with portable instruments for nondestructive testing accordingly has conventionally required rope access or sky platforms and cranes. This is time-consuming and possibly dangerous if the appropriate safeguards are not followed or if there is an equipment failure. Blade and tower crawlers with nondestructive testing sensors for in situ inspection have been developed and tested, again with high cost implications, slow inspection rates and questionable effectiveness. Microwave and radar scanners, while effective for dielectric materials, do not work on critical areas such as spar caps, which are often manufactured with electrically conductive carbon fiber materials.

New utility scale wind turbine blade designs are typically fatigue tested to failure at special facilities to accommodate the large size, often 50 meters span or more. Frequently, sensors such as fiber Bragg strain gages and acoustic emission (AE) sensors are bonded to the structures to allow monitoring during the entire test. While the use of acoustic emission (AE) sensors and technology is highly effective for detecting and locating propagating defects during ground based fatigue testing, standard AE practice requires bonding sensors to the blade throughout its span and in critical areas. The range of Rayleigh waves propagating in fiberglass is limited and multiple sensors are required raising cost and power requirements. Retrofitting the fleet of existing blades on wind generators in situ is a prospect both expensive and extremely hazardous.

Electricity generators designed to extract energy from the wind are powered by rotating turbines designed as either vertical axis wind turbines (VAWT) or horizontal axis wind turbines (HAWT). Large industrial scale power turbines are generally of the HAWT design using composite air foil shaped blades to generate the rotational torque needed to drive the electrical generator. Current utility scale wind turbine blades may range from 9 m in length up to more than 50 m, with much larger blades being designed for offshore wind power generators. The application of this invention may achieve good results on blades of all lengths.

A need accordingly exists for a cost effective wind turbine blade structural health monitoring system, both for the aging existing fleet as well as new wind turbines. There is a particular need for a wind turbine blade nondestructive testing system that is capable of performing testing and monitoring from the ground, and that is capable of providing remote notification or alerts as to the existence of propagating defects.

SUMMARY OF THE INVENTION

Accordingly, it is an object of the invention to provide a wind turbine blade structural health monitoring system and process that is cost-effective and capable of performing testing and monitoring from the ground, and that is capable of providing remote notification or alerts as to the existence of propagating defects.

In order to achieve the above and other objects of the invention, a wind power turbine blade inspection system according to a first aspect of the invention includes a sensor positioned on the blade root end bulkhead to receive airborne acoustic signals emanating from anomalies in rotating turbine blades during cyclic stress loading, a three axis accelerometer to determine the gravity vector and other sources of cyclic acceleration with respect to the acoustic signals and a signal analysis system configured to analyze the sensor and accelerometer signals to provide data for wind power asset management.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
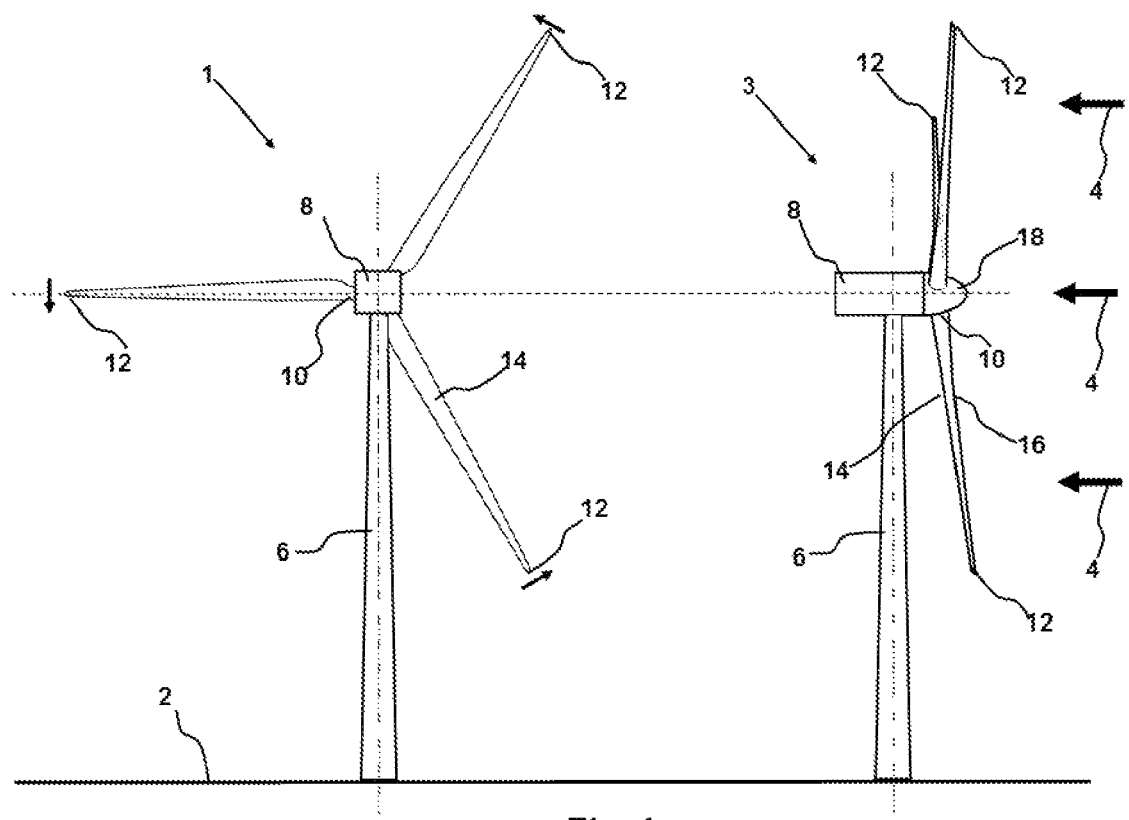
FIG. 1 is a schematic representation of a utility scale, horizontal axis, wind turbine generator.

Referring now to the drawings, wherein like reference numerals designate corresponding structure throughout the views, and referring in particular to FIG. 1, a wind turbine blade structural health monitoring system 1 according to a preferred embodiment of the invention is capable of continuously monitoring the structural health of both onshore and offshore power utility wind turbines for propagating defects or damage.

The system 1 is designed to monitor the structural integrity of utility scale wind turbine generator blades during operation. It includes of acoustic and accelerometer sensors, time signals, a data transmitter and power source positioned in the root of each blade to detect the airborne acoustic signal components of Rayleigh waves emitted by anomalies, latent manufacturing defects and damage during cycling stress loading of the blades in normal operation due to gravity and a data receiver/data analyzer mounted in a non-rotating location connected to the intranet, internet, cellular GSM, radio or other forms of digital communications to transmit reports of blade and turbine component conditions. This information is important for optimal wind power asset management, maintenance scheduling or turbine shut-down to prevent further damage, injury or even catastrophic failure.

The rapid release of energy from localized sources within the composite materials used to manufacture wind turbine blades generates surface elastic waves, or Rayleigh waves, that propagate within the solid material. These surface waves also known as acoustic emission (AE) events can generate airborne acoustic waves. While wave propagation in a compressible medium such as air is very different from that of a solid, such airborne signals are detectable from a distance and can be used to determine the onset of progressive damage to wind turbine blades during operation. In solids, acoustic emission events may be characterized by their waveform and can be analyzed by measuring peak amplitude, ring down count, time rise, event duration and energy as determined by the integration of the event waveform. Because solids are essentially incompressible and the speed of sound is high (3070 m/sec for composite carbon fiber/epoxy and 2740 m/sec for fiberglass) compared to that of air (approximately 345 m/sec), the conversion of surface waves to airborne acoustic waves, causes many of the characteristics of the Rayleigh waveform to be lost. However, airborne acoustic emission signals contain sufficient information, especially when analyzed with time synchronous accelerometer data to detect propagating latent defects and damage.

In one embodiment, sensor packages with a wireless data transmitter, a wide band microphone and an accelerometer are installed on each blade root end bulkhead. Powered by a small parasitic electrical generator and rechargeable battery, the acoustic data, 3 axis of acceleration data and the blade ID number are transmitted to a receiver in the generator nacelle for analysis and the transmission of the data, report or an alarm to the responsible entity for the operation of the turbine by way of the intranet, internet, CSM or other means. The present invention provides a means for low cost and safe retro-fit of the existing world fleet of wind turbines. In addition, including this apparatus during manufacturing provides full life cycle monitoring of the blade.

FIG. 1 is a schematic diagram of a HAWT that is typical of both land based and offshore turbine generators. The view 1 from behind the turbine facing the wind includes tower 6 extending up from the ground or ocean surface 2 to support the nacelle 8 which contains the generator and gear reducers, unless it is a direct drive generator. There are typically three blades on a utility scale wind turbine having root ends 10 and blade tips 21. As seen from the side view 2, the blade root ends attach to the rotatable hub 18. Blade side 16 facing the wind 4 is often referred to as the high pressure side. The blade side 14, facing away from the wind is referred to as the low pressure or suction side. As the blade speed increases the blade pitch is adjusted to the optimal angle of attack to the wind to create the maximum lift and torque required to drive the electricity generator.

Figure 2:
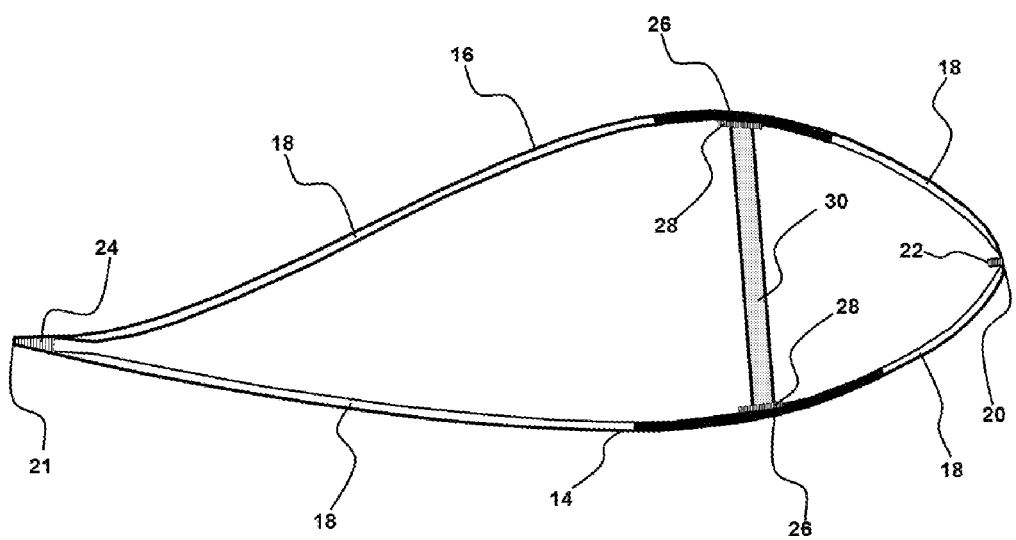
FIG. 2 is a schematic representation of a wind turbine blade cross section.

FIG. 2 shows the construction cross section of a typical HAWT blade. Wind turbine blades are generally manufactured with adhesively bonded composite shells forming the high pressure side 16 and the low pressure side 14. The trailing edge 21 is adhesively bonded as is the leading edge 20, with adhesive bonding in some cases between two flanges 22 formed by the inner and outer fiberglass skins that make up sandwich panels 18. Two spar caps 26, which may be made from fiberglass or carbon fiber laminate are bonded to the edges of the sandwich panels 18. The blade spar web 30, which can be a solid fiberglass laminate or a sandwich construction with fiberglass or carbon fiber face sheets and a core material made with foam, balsa wood or other suitable material with high compressive strength. The spar web 30 is bonded with adhesive 28 to the spar caps 26 to form an I beam. Sometimes a second or even third spar web is present forming a box beam. Defects such as adhesive disbonds or unbonds present at the spar cap 26 to spar web 30 adhesive bond 28 may lead to catastrophic failure of the blade in service. Fiber waves in the solid spar cap 26 laminate can also lead to cracking and ultimately to blade failure. Further, trailing edge 21 splits or cracks in the high pressure 16 and low 14 pressure side shell adhesive bond 24 may be signs or excessive blade flex during operation. The trailing edge 21 adhesive bond 24, in the area of greatest blade chord width towards the root end 10 supports blade twist loads. Cracks and breaks in the adhesive bond 24 at these locations can also lead to blade failure unless detected in time and the turbine shut down and promptly repaired. When one of the reinforcing elements such as a glass or carbon fiber breaks, it makes a distinct sound, like a stick breaking. The sound propagates throughout the structure of the wind turbine blade, and throughout the enclosed space defined by the interior surface of the outer skin of the blade. In addition, a pressure gradient develops within the enclosed space as a result of centripetal acceleration. The pressure differential between the portion of the enclosed space that is proximate the wind turbine hub and the outermost portion of the enclosed space can be on the order of 2 psi.

Figure 3:
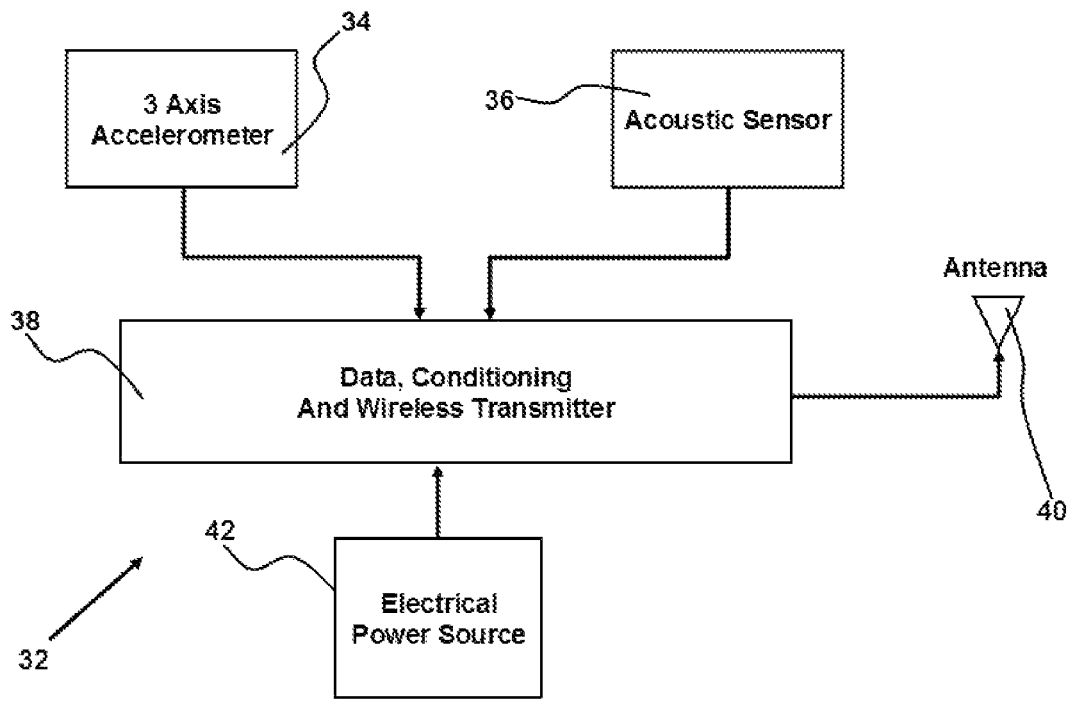
FIG. 3 is a block diagram of the sensor package fitted to each blade bulkhead in accordance with an embodiment of the invention.

FIG. 3 is a block diagram of the blade mounted sensor device 32 that is installed in the root end 10 of each blade. The device 32 comprises a 3-axis accelerometer 34, an acoustic sensor 36, a data conditioning and formatting circuit 38 which includes a wireless transmitter with antenna 40. The acoustic sensor 36 is preferably coupled to the enclosed space defined within the wind turbine blade, and is preferably positioned at or proximate to the outermost end of the enclosed space. The device 32 is power by a parasitic electricity generator and a rechargeable battery 42. The parasitic generator 42 extracts energy from the rotating turbine blade to which it is attached. The accelerometer 34, measures the angle of the blade it is attached to with respect to the gravity vector. When the blade is located at ninety degrees from the vertical, or $\pi/2$ radians, the force of gravity exerting torque on the blade is at it's maximum, at 180 degrees, or $\pi$ radians, the torque due to gravity is zero, and at 270 degrees, or $\pi/2$ radians, the torque is at it's maximum negative value.

The position of each blade with respect to the gravity vector as determined by the accelerometer 34, may be used to correlate the position of the blade with the time when airborne acoustic emission signals are detected and to compare for each blade rotation phase angle when acoustic emission signals from each of the other two blades are detected. The blade data may be designed also that the serial number of each blade is encoded in the wireless data transmission allowing identification of the specific blade that producing signals that are out the acceptable range. The data in each sensor device may be transmitted continuously and simultaneously from each blade on different frequencies, in time sequential compressed packets or any other data transmission scheme designed to reduce both cost and power consumption requirements for power from generator 42.

Figure 4:
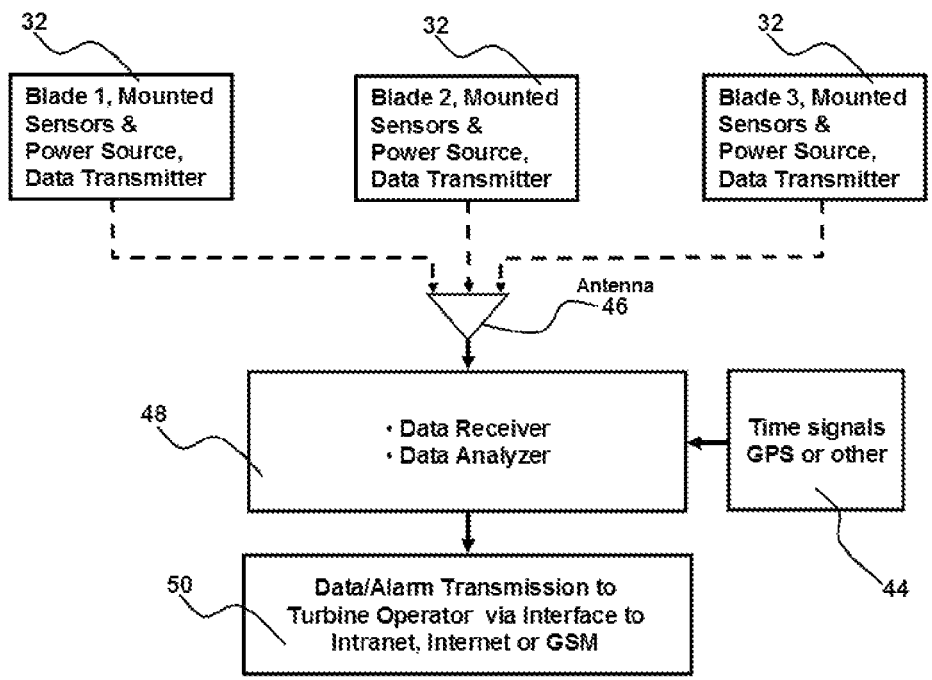
FIG. 4 is a block diagram of the data receiver/analyzer mounted in the generator nacelle in accordance with an embodiment of the invention.

FIG. 4 is a block diagram of the tower or nacelle mounted data receiver and analyzer device 48. The purpose of this device is to receive data transmissions from the sensors 32 in each blade root end 10 by way of a wireless signal. Time signals provided by a GPS receiver or other source of accurate time signals, 44, are used to determine the timing of AE events and to allow comparison of acceleration signals from the 3 axis accelerometers 34, in each sensor package 32, to determine and compare the condition and performance each blade with respect to the others on the turbine. For example, continuously variable pitch blades have been recently introduced. The timing and amount of blade pitch changes for each blade can be measured during operation and anomalies detected. In addition, the data analyzer 48 use algorithms designed to detect the propagation of latent defects or damage to the blade and transmit the data to a central location, format and transmit an alarm or a report to the responsible entity by way of the intranet, the internet or by GSM cellular radio or other means of secure data transmission.

Figure 5:
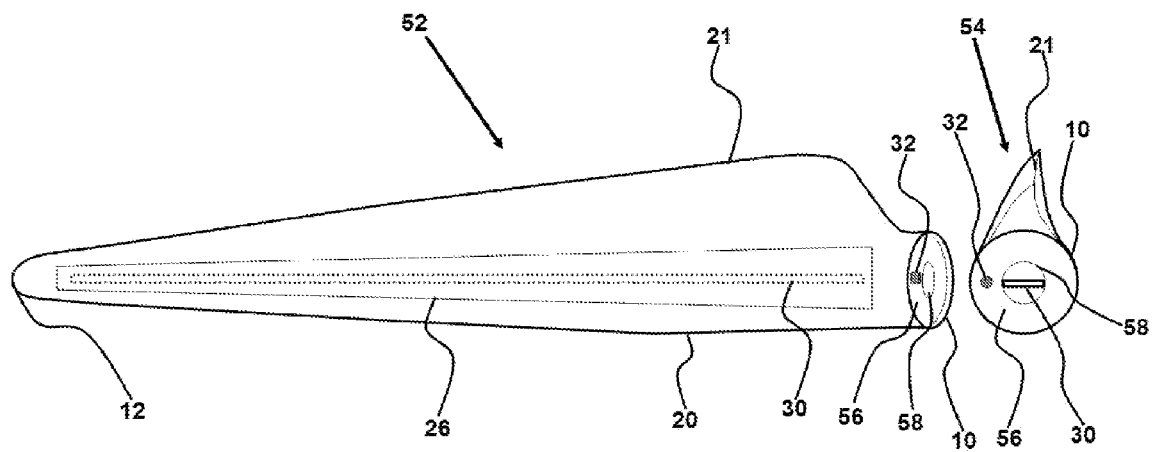
FIG. 5 is an illustration of a wind turbine blade showing the sensor package mounting location on the root end bulkhead in accordance with an embodiment of the invention.

FIG. 5 shows the approximate location of the blade sensor device 32, mounted preferably on the end bulkhead 56, just inside the root end 10 of the blade 52. Usually this bulkhead 56 is plywood or fiberglass both of which are easy to drill and can be used to mount hardware using screws or other appropriate fasteners. The position of the sensor 32 should be medial with the spar web 30 to allow airborne acoustic emission signals from sources on both the leading edge 20 and trailing edge 21, to be received by the sensor 60 and on either side of the access hole 58 in bulkhead 56. To install the sensor, a workman climbs into the turbine hub 18, a regular maintenance procedure to reach the blade pitch actuators for servicing. A hole is drilled through bulkhead 56 to allow the microphone components of the sensor package 32 to receive acoustic signals originating from inside the blade 52. In operation, sensor package 32 is powered by a small parasitic electricity generator using any one of a variety of technologies available including weighted piezoelectric generator, weighted pendulum on a small generator or alternator and a falling magnet and coil designed to extract energy from the rotating turbine using gravity.

Sensor package 32 is preferably a broad band acoustic sensor to detect the airborne component of Rayleigh waves from propagating defects, a three axis accelerometer to detect blade motion with respect to gravity and tower motion, a short range radio transmitter all powered by a small parasitic generator. Preferably, it has a frequency response that is substantially within a range of about 100 Hz to about 80 kHz. The sensor package 32 is preferably built into a sturdy enclosure with attachment points for mounting in the blade root end bulkhead in such a manner as to provide stability and direct communication for the sensitive portion of the acoustic sensor with the air inside the blade. Further, the internal blade shape causes the acoustic signals to be directed towards the root end of the blade and the acoustic sensor. The acoustic sensor must be designed to be protected from debris inside the blade consisting primarily of cured adhesive.

Figure 6:
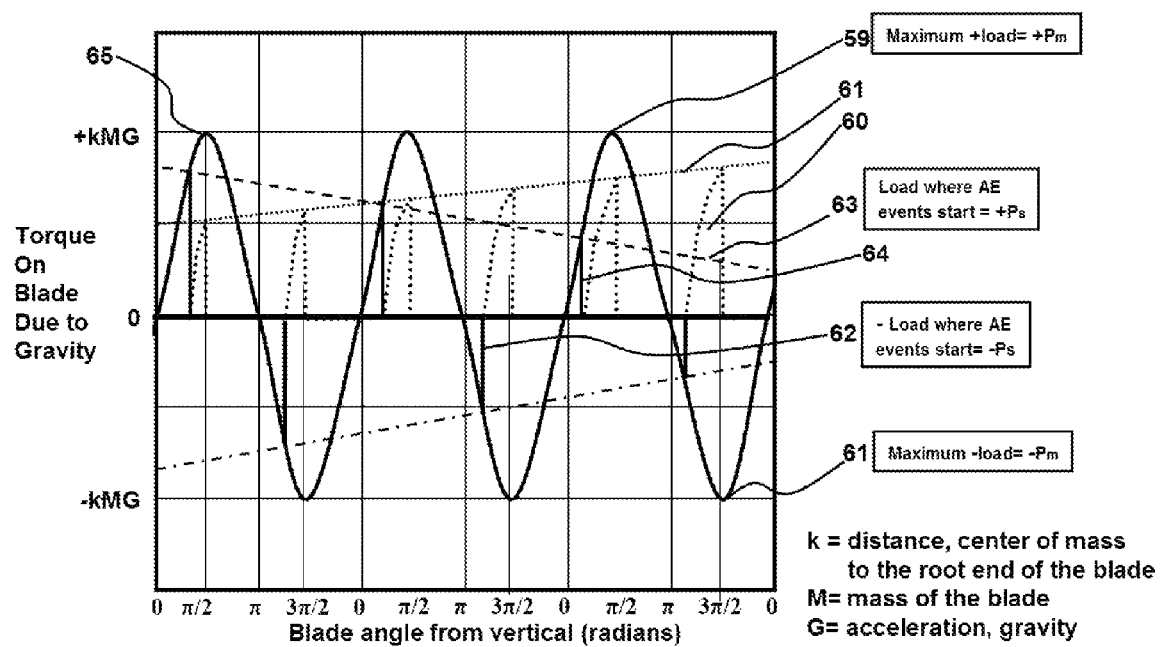
FIG. 6 is graphical plot showing the relationship between blade angle, torque on the blade, the onset of acoustic emission signals and the increasing amount of AE signals and decreasing Felicity ratio expect of a blade with propagating defects.

FIG. 6 is a schematic diagram showing the relationship between the blade angle $\alpha$ from the vertical position, and the torque acting on the blade during rotation of the turbine. The output 60 of one channel of the 3 axis accelerometer sensor 34 in sensor package 32 which is detecting the gravity vector. The accelerometer detects the acceleration due to the gravity vector which, over time, is a sine wave varying in frequency with the period of the turbine. With the blade point straight up at a blade angle of 0 radians from the vertical, the torque load due to gravity on the blade is 0. The torque can be represented by the equation $T = kM \sin \alpha G$, where k is the distance from the center of mass of the blade to the blade root end, M is the mass of the blade, G is the acceleration due to gravity and $\alpha$ is the angle of the blade from the vertical position. The torque acting on the blade peaks at 90 degrees from the vertical or $\pi/2$ radians and again at 270 degrees from the vertical at $\pi/2$, 66 and 68. These peak loads are in the opposite direction, effectively imparting a reversing fatigue load on the blade. Acoustic emission signals may be generated as the positive and negative loads cycle during blade revolution.

Also shown is the increasing number 72 and 76, of acoustic emission events over time emanating from the propagation of defects within the blade. In addition, also shown is the decreasing load level or torque 70 and 74 acting on the blade where acoustic emission events begin as compared to previous loads in the turbine rotational cycle. This effect, known as the Felicity ratio is defined as $(F_R)$=Load where AE start to occur on a successive stress cycle/Maximum Load during the previous stress cycle. As cracks begin to propagate over time due to the cyclic gravitational loading of the blade the number of acoustic emission events per blade revolution, 72 & 76 increases. Further, the stress or load level at which AE starts is slightly reduced for each revolution as the stress becomes concentrated in the crack tips. This reduction in the Felicity ratio over time, 78, as well as the increase in the number of AE events per revolution or during equal number of revolutions over time, 80, may be used as a trigger to alert signal to the wind generator owner/operator that a defect is growing and the blade requires attention. Comparison of the AE signal rates between blades may also be used to detect an outlier blade with the onset of propagating damage prior to a catastrophic failure.

Further, the 3 axis accelerometer, 34, in each sensor package, 32, coupled with accurate time signals from a GPS sensor or other accurate time signal source, can be used to compare the motion of each blade on a tower to detect blade pitch actuation anomalies, excessive vibration or motion due to loosening blade attachment nuts and the presence of ice on the blades creating an unbalanced condition.

While the preferred embodiment of the invention utilizes a 3-axis accelerometer, the invention could also be practiced using a 1-axis accelerometer or a 2-axis accelerometer.

Figure 7:
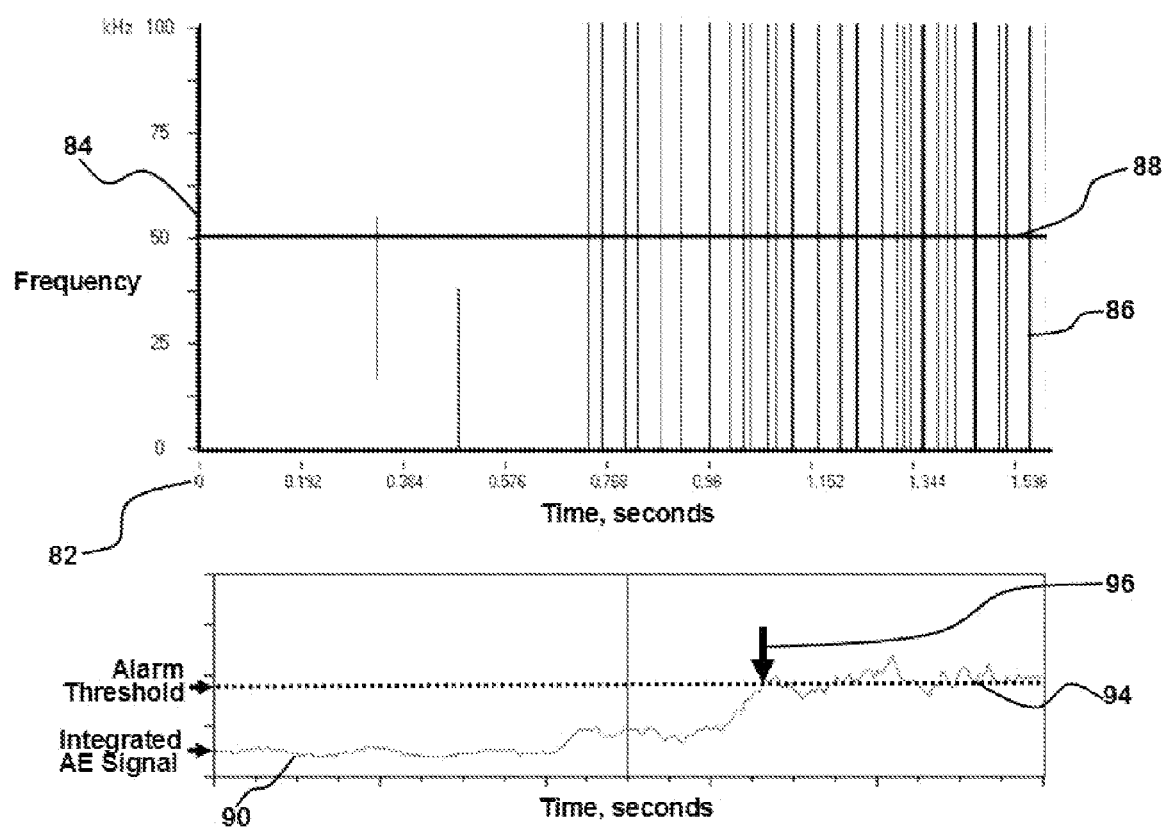
FIG. 7 shows two graphical plots of acoustic emission signal increasing in time and an alarm threshold.

FIG. 7 shows a plot of airborne acoustic emission events 86, recorded at the onset of loading a wind turbine blade section during a fatigue test. This plot may be similar to one showing AE signals emitted from a blade as it moves from a "no load" position at the 0 radian to the $\pi/2$ position where the blade experiences maximum load due to gravity. The signals can be filtered by frequency to eliminate sounds from actuators and machinery. As shown, a High Pass frequency filter 88, is set to pass only signals above 50 kHz. The AE signals, while having a short duration measured in microseconds are representative of the release of energy. Summing the area under the signals waveform and plotting the resulting curve yields a representation of the strain energy release 90, over time. An alarm threshold 94, can be set which can be used to trigger an alarm 96, or as a data point along with other measurements to trigger an alarm.

Figure 8:
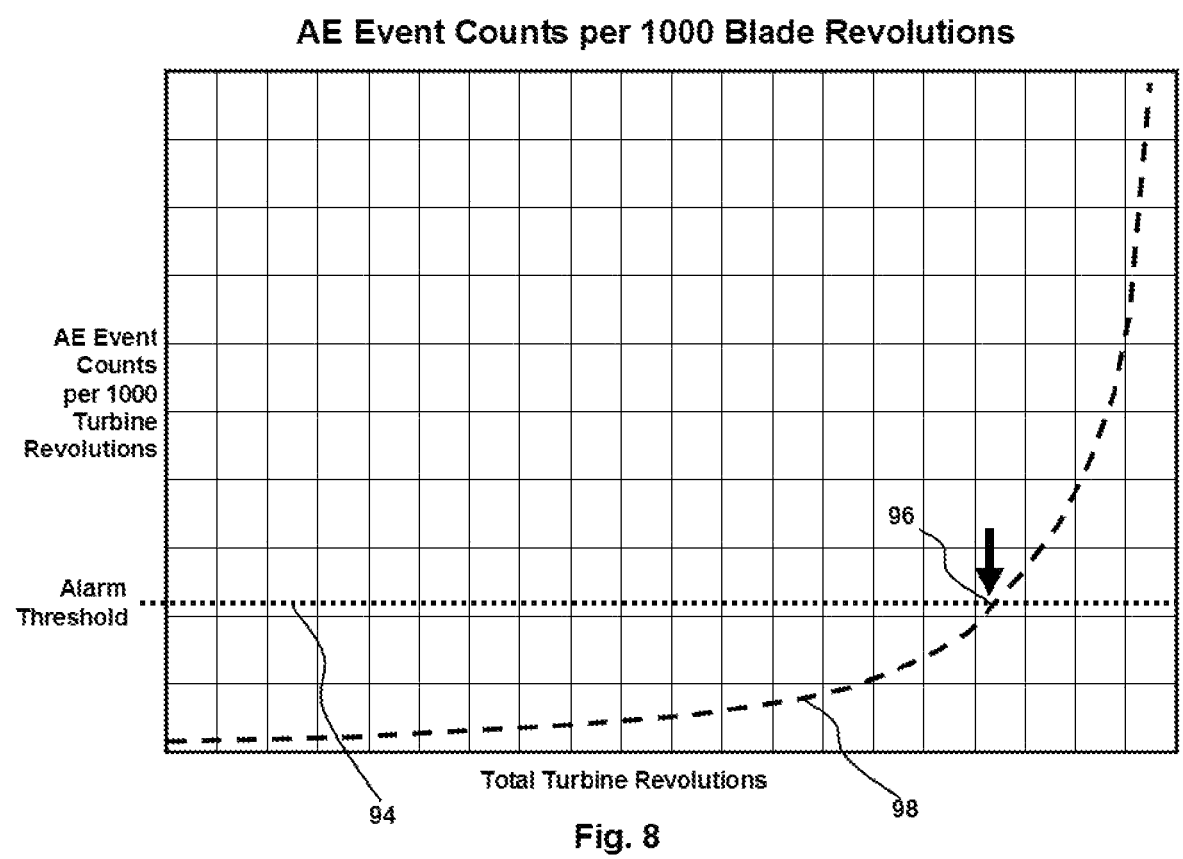
FIG. 8 is a graphical plot showing the increasing acoustic emission event count per 1000 turbine revolutions as latent defects or damage propagate inside a blade. An alarm threshold is set to trigger an alert when the rate exceeds a threshold level.

FIG. 8 shows a second plot of AE events per 1000 blade rotations. If latent defects or damage to a blade is great enough, stress risers will cause the defect to grow and ultimately fail. The quantity of AE signals 98, increases as the area of the defect(s) increases over time. Eventually the blade fails. An alarm level 96, is set for a specific count/1000 revolutions.

The health monitoring system architecture may be design in a number of different ways to achieve the same end of using blade mounted sensors to monitor the structural health of wind turbine blades. For example, data from each blade can be compared with data from each sensor package in the other blades. For example, the number of acoustic emission events per number or revolutions or unit of time may be used to detect a blade with propagating defects.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of detecting defects in a wind turbine blade, comprising steps of:

detecting, during motion of the wind turbine blade, a position, over time, of the wind turbine blade with respect to a gravity vector;

detecting, within an enclosed space of the wind turbine blade, acoustic information that is emitted from the wind turbine blade; and analyzing the acoustic information in conjunction with the position, over time, of the wind turbine blade to identify a potential defect in the wind turbine blade.

2. A method of detecting defects in a wind turbine blade according to claim 1, wherein the step of detecting the position, over time, of the wind turbine blade is performed using an accelerometer.

3. A method of detecting defects in a wind turbine blade according to claim 2, wherein the accelerometer is a three axis accelerometer.

4. A method of detecting defects in a wind turbine blade according to claim 2, wherein the accelerometer is mounted on the wind turbine blade.

5. A method of detecting defects in a wind turbine blade according to claim 4, wherein the accelerometer is constructed and arranged to provide identification data that permits identification of the wind turbine blade on which the accelerometer is mounted.

6. A method of detecting defects in a wind turbine blade according to claim 1, further comprising a step of transmitting data related to the position, over time, of the wind turbine blade wirelessly.

7. A method of detecting defects in a wind turbine blade according to claim 1, wherein the step of detecting acoustic information is performed remotely from a remote distance.

8. A method of detecting defects in a wind turbine blade according to claim 1, wherein the step of analyzing acoustic information in conjunction with the motion position, over time, of the wind turbine blade is performed using a computer.

9. A method of detecting defects in a wind turbine blade according to claim 8, wherein the computer is positioned on the wind turbine blade and powered using a parasitic electrical generator that is also positioned on the wind turbine blade.

10. A method of detecting defects in a wind turbine blade according to claim 1, wherein the step of analyzing the acoustic information in conjunction with the position, over time, of the wind turbine blade comprises correlating the acoustic information with the position of the wind turbine blade at a specific time.

11. A method of detecting defects in a wind turbine blade according to claim 10, further comprising a step of obtaining time information from a remote source.

12. A method of detecting defects in a wind turbine blade according to claim 11, wherein the remote source is a GPS satellite.

13. A method of detecting defects in a wind turbine blade according to claim 1, further comprising steps of obtaining acoustic and position, over time information with respect to at least one additional wind turbine blade, and comparing information from the respective blades to identify an outlier blade.

* * * * *